United States Patent [19]

Sasaki et al.

[11] Patent Number: 5,410,914
[45] Date of Patent: May 2, 1995

[54] MEASURING DEVICE FOR DENSITY OF LIQUID OR HIGH-TEMPERATURE MELT WITHOUT INFLUENCE OF SURFACE TENSION

[75] Inventors: Hitoshi Sasaki, #A-101 Pakusaidokawamura, 42-2, Kasuga 2-chome, Tukuba-shi, Ibaragi-ken, Japan, 305; Eiji Tokizaki, Ibaragi, Japan; Kazutaka Terashima, 206-3, Nakano, Ebina-shi, Kanagawa-ken, Japan, 243-04

[73] Assignees: Research Development Corporation of Japan, Tokyo; Hitoshi Sasaki, Tukuba; Kazutaka Terashima, Ebina, all of Japan

[21] Appl. No.: 137,764

[22] Filed: Oct. 19, 1993

[30] Foreign Application Priority Data

Nov. 2, 1992 [JP] Japan ............................ 4-317900

[51] Int. Cl.⁶ .............................................. G01N 9/10
[52] U.S. Cl. ........................................ 73/437; 73/433; 73/434; 73/435; 73/436
[58] Field of Search .................. 73/433–437, 73/438, 435–450; 43/42.36, 43.1

[56] References Cited

U.S. PATENT DOCUMENTS

| | | | |
|---|---|---|---|
| 1,412,884 | 4/1922 | Midgley, Jr. | 73/440 |
| 3,747,416 | 7/1973 | Wommack | 73/437 |
| 4,485,675 | 12/1984 | Verret | 73/439 |
| 4,621,447 | 11/1986 | Rhodes | 43/17.5 |
| 5,097,616 | 3/1992 | Johnston, Jr. | 43/4 |
| 5,129,178 | 7/1992 | Hicks | 43/44.87 |

Primary Examiner—Richard E. Chilcot, Jr.
Assistant Examiner—Max H. Noori
Attorney, Agent, or Firm—Nikaido, Marmelstein, Murray & Oram

[57] ABSTRACT

The measuring device has bobs 10, 17 suspended from a weight 12 with wires 11, 16. The hook 13 of the weight 12 is hung from a suspensor thread 15 extending downwards from a balance 14. The weight 12 may be omitted by using the upper bob 10 for dead weight. The bobs 10, 17 and the wires 11, 16 may be coated with a coating layer unreactive to the melt 19 whose density is to be measured. The weights of the measuring device is measured by the balance 14 under the first condition that the lower bob 17 is immersed in the liquid 19 and the second condition that the bobs 10, 17 are both immersed in the liquid 19. The density of the liquid 19 is calculated from the two measured values without the influence of the surface tension of the liquid 19 applied to the wires 11, 16.

10 Claims, 5 Drawing Sheets

MEASURING DEVICE FOR DENSITY OF LIQUID OR HIGH-TEMPERATURE MELT WITHOUT INFLUENCE OF SURFACE TENSION

BACKGROUND OF THE INVENTION

The present invention relates to a measuring device suitable for measuring the density of a liquid such as a high-temperature melt. This measuring device is especially useful for receiving the density information of a semiconductive compound or metal melt which has substantial influences on crystal growth from the liquid phase.

A semiconductor device exhibits better performances as functions are integrated with higher density. The demand for the improvement of a semiconductor substrate in quality becomes stronger in response to the high-density integration. In order to develop the technical field of semiconductors, there are urgently required the settlement of the method which can control the inclusion of defects into a semiconductive crystal as well as the method which can manufacture a single crystal large in diameter for the enhancement of production efficiency.

The inclusion of defects in a semiconductive crystal is largely influenced by the liquid state of a melt. However, the liquid state of the melt is not yet made completely clear, since there is not an effective means for measuring the property of the high-temperature semiconductor melt with high accuracy in a short time.

The density of a high-temperature semiconductor melt is one of the factors which have large influences on the formation of defects in crystals.

Archimedes' method, i.e. a representative method for measuring the density of a liquid, uses the measuring device which has a bob 1 hung down with a suspensor wire 2, as shown in FIG. 1. The bob 1 is dipped in a liquid 3 whose density is to be measured. The weight of the bob 1 being dipped in the liquid 3 is measured by a balance 4. The density $\rho$ of the liquid 3 is calculated from the measured values according to the formula of:

$$\rho = (M_v - M_1)/V_b$$

wherein $V_b$ represents the volume of the measuring device to be dipped in the liquid 3, $M_v$ represents the weight of the measuring device measured by the balance 4 in a vacuum atmosphere, and $M_1$ represents the weight of the measuring device dipped in the liquid 3.

The volume $V_b$ is previously detected by measuring the weight of the measuring device dipped in the liquid, e.g. water, whose precise density is already known. Hereby, the density $\rho$ of the liquid 3 is obtained from the difference between the weight $M_v$ in vacuo and the weight $M_1$ in the dipped state.

However, various errors originated in the properties of the liquid and the bob as well as a surface phenomenon are likely included in the measuring result obtained by Archimedes' method.

For instance, there is a surface tension between the suspensor wire 2 hanging the bob 1 and the liquid 3. Due to the surface tension, the surface of the liquid 3 in contact with the suspensor wire 2 is partially reformed into the state as shown in FIG. 2, so that the measuring device is affected by the upward force which makes the measuring result larger.

In case where the liquid 3 is heated at a high temperature by a heater provided around a crucible 6, a convection current is thermally formed in the liquid 3, as shown in FIG. 3. The descending flow at the central part applies a downward force to the bob 1, so that the measuring result is made smaller. In order to avoid the influence of the thermal convection 5, it is necessary to interrupt the heating of the liquid 3. As a result, it is difficult to measure the density of the liquid 3 at a constant temperature.

Besides, since the weight is measured under the condition that the bob 1 is dipped in the liquid 3, the bob 1 shall have apparent density larger than the density of the liquid 3. Otherwise, the bob 1 would float on the surface of the liquid 3, so that the density of the liquid 3 could not be measured. In addition, the bob 1 shall have a surface excellent in wettability to the liquid 3 and chemically stable against the attack of the liquid 3, and the bob 1 shall be made of a heat-resistant material which is not deformed by the heat of the liquid 3. Consequently, the bob 1 does not endure use for a long time, and there are various limitations on the material of the bob 1.

SUMMARY OF THE INVENTION

An object of the present invention is to overcome the defects abovementioned by using a new measuring device which has a bob coupled with a weight by a connector.

Another object of the present invention is to measure the density of a high-temperature semiconductor or metal melt with high accuracy.

According to the present invention, there is provided a new measuring device which has a bob or bobs coupled with a weight by a connector such as a wire or rod. The coupling of the bob and the weight enables measuring the density of a liquid or high-temperature melt cancelling the influence of surface tension. A hook extending upward from the weight is hung from the arm of a balance. In case where two bobs are connected together, the weight may be omitted by using the upper bob also as a dead weight.

The bob is accurately directed downwards and kept in the attitude capable of dipping along a vertical direction. Hereon, a descending motion is applied to the bob using a rigid wire or rod, so that a bob made of a material having smaller specific gravity can be dipped in the liquid whose density is to be measured.

The bob and the wire are preferably coated with a layer unreactive to the liquid. The wettability of the bob to the liquid can be controlled by the selection of the coating material. In addition, the coating layer applies effective rigidity to the bob suitable for dipping the bob in the liquid along the vertical direction. When a rod having high rigidity is used instead of the wire, the bob is lowered and dipped in the liquid along the vertical direction regardless the difference in specific gravity between the bob and the liquid. In case where a wire is used in a naked state uncoated with the coating layer, the wire is preferably made of a material excellent in heat resistant against the heat of the liquid.

DETAILED DESCRIPTION OF THE PREFERRED EMBODIMENTS

Figure 1:
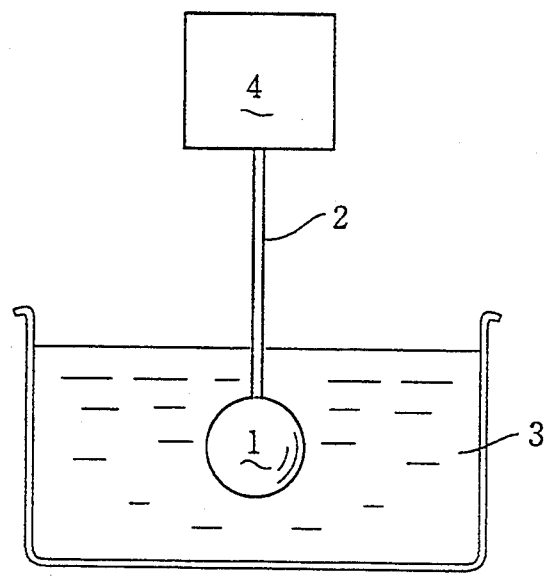
FIG. 1 is a schematic view illustrating a conventional measuring device for measuring he density of a liquid according to Archimedes' method.
Figure 2:
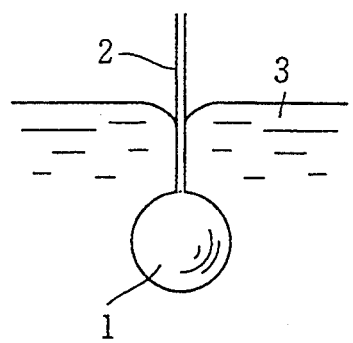
FIG. 2 is a view for explaining the influence of surface tension in Archimedes' method.
Figure 3:
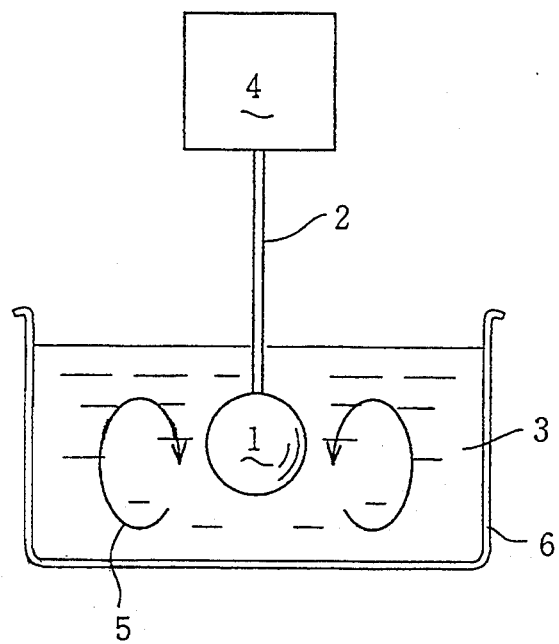
FIG. 3 is a view for explaining the influence of convection thermally formed in the liquid.
Figure 4:
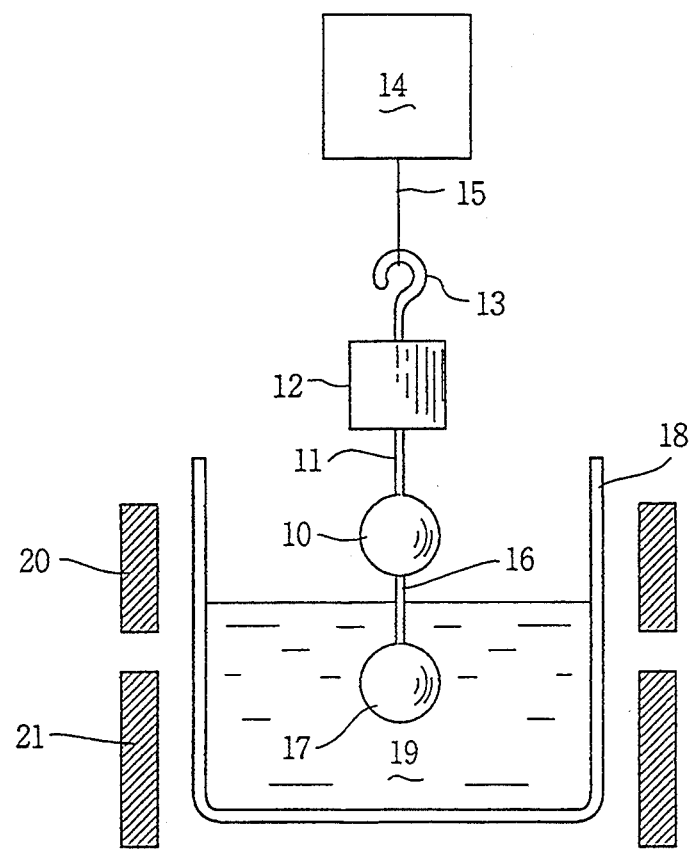
FIG. 4 is a schematic view illustrating the situation for measuring the density of a liquid using a new measuring device according to the present invention.

The measuring device according to the present invention has a bob 10 coupled with a weight 12 by a connector such as a wire 11. A hook 13 extending upward from the weight 12 is hung from a suspensor thread 15 descending from a balance 14. Another bob 17 may be attached to the bob 10 by a lower wire 16.

The measuring device is lowered to the position where the bob 10 is immersed in the melt 19 whose density is to be measured. A crucible 18 for receiving the melt 19 is surrounded with an upper heater 20 and a lower heater 21. These heaters 20, 21 are individually controlled so as to form a preferable temperature gradient in the melt 19. The convection, which is likely to be thermally formed in the melt 19 received in a crucible 18, is inhibited by controlling the heating powers of the heaters 20, 21. For instance, the heating power of the upper heater 20 is made larger, so that the upper part of the melt 19 is kept at a higher temperature compared with the lower part.

The bobs 10, 17 and the wires 11, 16 are preferably coated with the material 23 which does not react with the melt 19. The selection of the coating material 23 enables the application of the measuring device even to the melt 19 which is reactive to the substrate material of the bobs 10, 17 and the wires 11, 16. Owing to the coating, the bobs 10, 17 can be made of various material with the high degree of freedom, too. Hereby, a cheap material easy to reform to an objective shape may be used in response to the purpose.

The kind of the coating material 23 is selected taking into consideration the kind of the melt 19 whose density is to be measured. For instance, boron nitride, silicon carbide, sialon, aluminum nitride, silicon nitride, carbon, platinum, silica-alumina complex may be used as the coating material 23. The measuring device can be provided with a resistance to the corrosive or erosive melt 19 by the selection of the coating material 23. Hereby, the measuring device according to the present inventions can be used for easily measuring the density of various melts or liquid.

Figure 5:
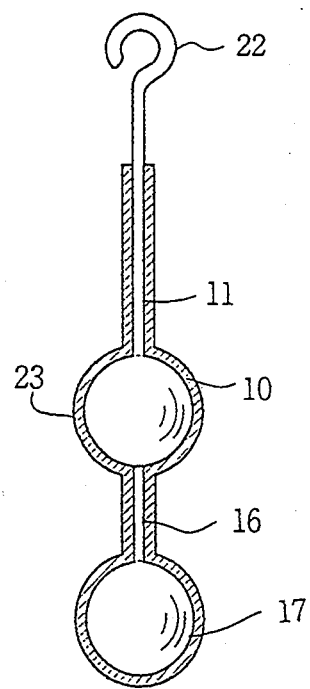
FIG. 5 is a sectional view illustrating an example of the measuring device according to the present invention.

When two bobs 10, 17 are coupled together, the upper bob 10 serves as a weight, too. Hereon, the weight 12 can be omitted. In this case, a hook 22 is formed at the upper end of the wire 11 extending upwards from the upper bob 10, as shown in FIG. 5.

When the measuring device having two bobs 10, 17 coupled together is used for measuring the density of the melt 19 for instance, errors originated in the surface tension of the melt 19 affecting on the wire 16 is cancelled by the following reason.

The weight $M_s$ of the measuring device under the condition that the lower bob 17 only is dipped in the melt 19 is calculated according to the formula of:

$$M_s = M_v \rho V_1 + F_s \tag{1}$$

In the formula (1), $F_s$ represents the surface tension applied to the wire 16, $V_1$ represents the volume of the lower bob 17 including the part of the wire 16 immersed in the melt 19, $\rho$ represents the density of the melt 19, and $M_v$ represents the weight of the measuring device in vacuo.

On the other hand, the weight $M_d$ of the measuring device under the condition that the bobs 10, 17 are both dipped in the melt 19 is calculated according to the formula of:

$$M_d = M_v - \rho(V_1 + V_2) + F_s \tag{2}$$

In the formula (2), $V_2$ represents the volume of the upper bob 10 including the parts of the wires 11, 16 immersed in the melt 19.

When the surface tension $F_s$ is eliminated from the formulas (1) and (2), the formula (3) is obtained. Thus, the density $\rho$ of the melt 19 is calculated with high accuracy according to the formula (3), without the influence of the surface tension $F_s$.

$$\rho = (M_s - M_d)/V_2 \tag{3}$$

EXAMPLE 1

A high-purity Ge material was received in a graphite crucible 18 surrounded with a couple of upper and lower resistant heaters 20, 21. A melt 19 was prepared by heating and melting the Ge material with the heaters 20, 21. Hereon, the heating powers of the upper heater 20 and the lower heater 21 were independently controlled so as to hold the upper and lower parts of the melt 19 at 1150° C. and 1140° C., respectively.

The density of the melt 19 was measured using the measuring device (shown in FIG. B) having two bobs 10, 17 coupled together with a wire 16. A hook 22 was formed at the upper end of a wire 11 extending upwards from the upper bob 10. The surface parts of the bobs 10, 17 and the wires 11, 16 to be dipped in the melt 19 were coated with a boron nitride coating layer 23. The hook 22 was hung from the suspensor thread 15 descending from a balance 14.

Mo balls each of 1.1 cm$^3$ in volume $V_2$, $V_1$ were used as the bobs 10, 17. Mo wires of 0.8 mm in diameter cut to length of 100 mm and 10 mm were used as the wires 11 and 16, respectively. These wires 11, 16 had enhanced rigidity owing to the boron nitride layer 23.

The weight $M_v$ of the measuring device comprising the bobs 10, 17 and the wires 11, 16 was measured in a vacuum atmosphere. The weight $M_v$ was 41.3878 g.

The measuring device was dipped in the melt 19 until the wire was partially immersed with the depth of 5 mm. The lower bob 17 was completely sunk in the melt 19. Hereon, the weight $M_s$ of the measuring device measured by the balance 14 was 34.9343 g.

The measuring device was further lowered until the wire 11 was partially immersed with the depth 5 mm. Hereby, the bobs 10, 17 were both Completely immersed in the melt 19. The weight $M_d$ of the measuring device measured by the balance 14 was 28.8417 g.

The weights $M_s$, $M_d$ and the volume $V_2$ in the formula (3) were substituted by the measured values to calculate the density $\rho$ of the melt 19. The result was $\rho = 5.3675$.

Figure 6:
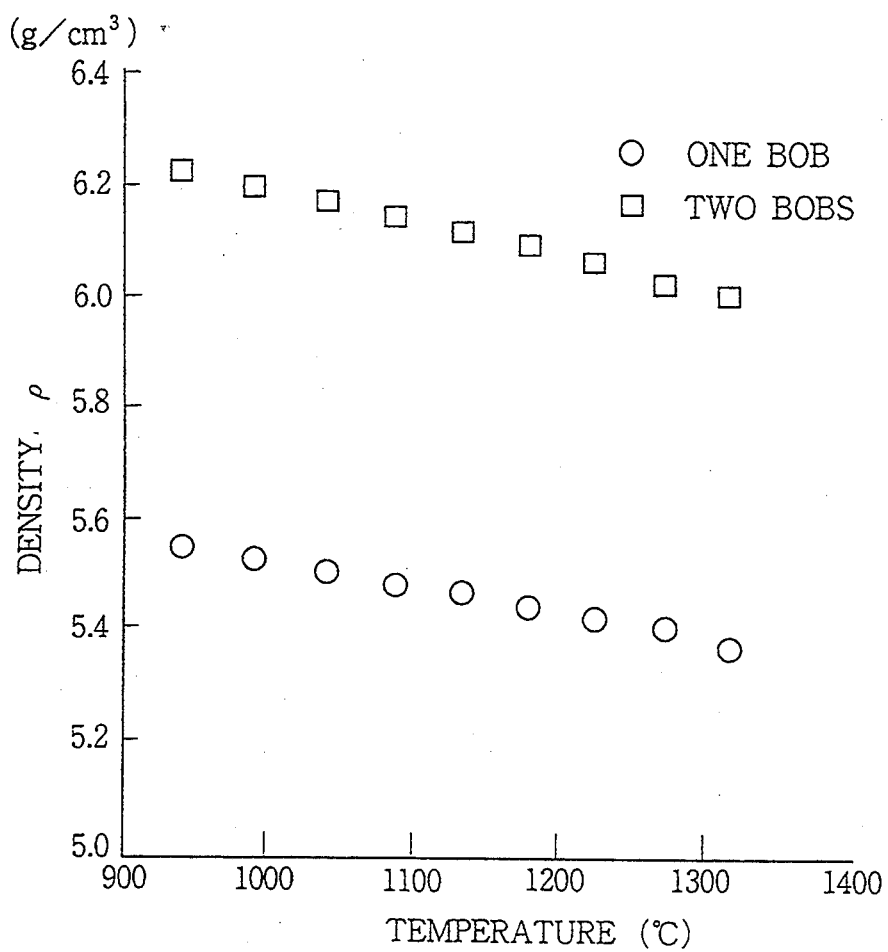
FIG. 6 is a graph showing the relationship between the density of Ge melt and the temperature.

The density $\rho$ of the melt 19 was repeatedly measured several times in the same way. The deviation of the measured values was within a very small range of $\pm 6.6 \times 10^{-4}$. Hereby, it is recognized that the density of the melt 19 can be detected with high accuracy according to the present invention. The density $\rho$ measured in this way had the relationship with the temperature of the melt 19, as shown in FIG. 6.

As for comparison, the density of the same melt 19 was measured using one bob 1 (shown in FIG. 1) without using the weight 12. In this case, the measured value was higher by 10% than a value reported in available documents.

It is apparent from the comparison that the density of the melt is measured with high accuracy and reliability according to the present invention.

EXAMPLE 2

A high-purity Si material was received in a crucible 18 made of boron nitride. After a melt 19 was prepared by heating and melting the Si material, the temperature distribution of the Si melt was controlled.

Figure 7:
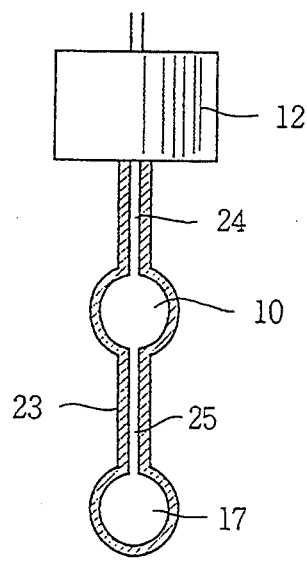
FIG. 7 is a view illustrating another example of the measuring device according to the present invention.

The density of the Si melt prepared in this way was measured using a measuring device shown in FIG. 7. In this measuring device, bobs 10, 17 and a weight 12, each made of graphite, were connected with each other by rigid rods 24, 25, and the whole surface was coated with a boron nitride layer 23. Owing to the rigid rods 24, it was able to lower the bobs 10, 17 along the accurately vertical direction regardless the difference in specific gravity between the melt 19 and the bobs 10, 17.

The weight $M_v$ of the measuring device measured in a vacuum atmosphere was 23.8545 g. The weight $M_s$ of the measuring device measured by the gravity balance 14 under the condition that the lower bob 17 was immersed in the melt was 21.1862 g. The weight $M_d$ of the measuring device under the condition that the upper bob 10 as well as the lower bob 17 were immersed in the melt 19 was 18.6299 g.

The weights $M_s$, $M_d$ and the volume $V_2$ in the formula (3) were substituted by the measured values to calculate the density $\rho$ of the melt 19. The result was $\rho = 2.5220$.

The same measuring was repeated several times. The deviation of the measured values was within the very small range of $\pm 7.9 \times 10^{-4}$. The resulting density $\rho$ had the relationship with the temperature of the melt 19, as shown in FIG. 8.

Figure 8:
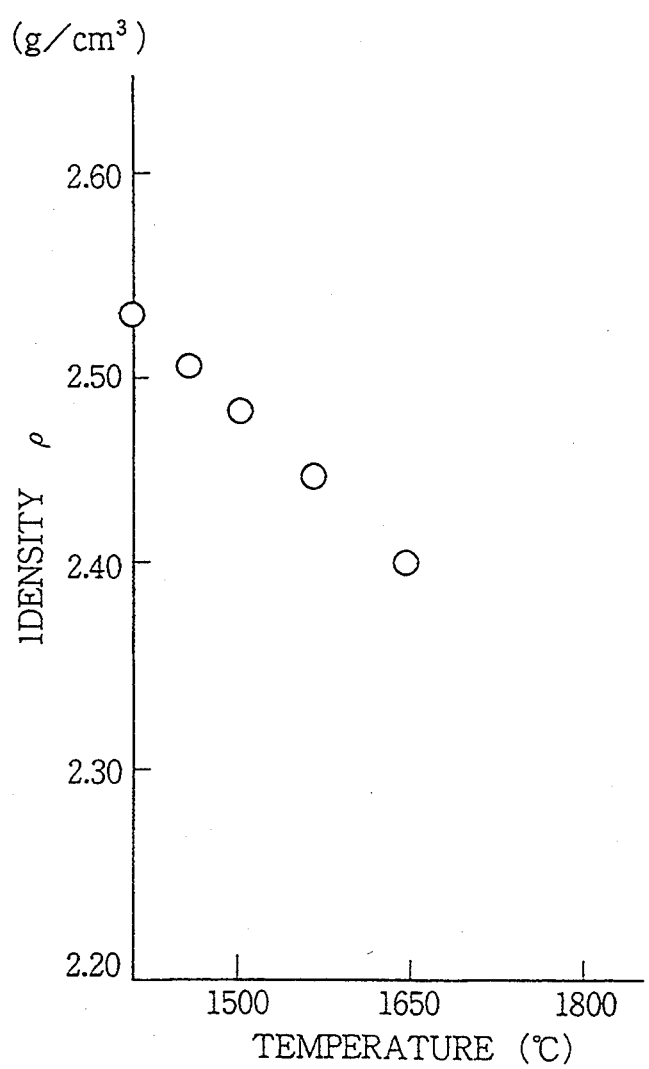
FIG. 8 is a graph showing the relationship between the density of Si melt and the temperature.

The relationship between the density and the temperature, as shown in FIG. 6 or FIG. 8, is useful for detecting the state of a liquid or a high-temperature melt. For instance, the gradiation of a temperature in the melt 19 necessary for stable crystal growth can be made clear from the changing of the density. A thermal convection in the melt 19 can be detected from the changing of the density, too.

In the examples abovementioned, the measuring device according to the present invention was used for measuring the densities of Ge and Si melts. However, the examples do not have any limitations on the scope of the present invention. The present invention may be applied for measuring the density of similar material or a liquid having relatively large specific gravity in the same way.

According to the present invention as abovementioned, the bob of a measuring device is forcibly dipped in a liquid or melt whose density is to be measured. Hereby, the density of the liquid or melt is measured with high accuracy, even when the liquid or melt has specific gravity larger than that of the bob inferior in wettability to the liquid or melt. Since the density is calculated without the influence of the surface tension of the melt or liquid applied to the bob, the measured value represents the density of the melt or liquid with high reliability. In addition, the density of a corrosive or erosive melt can be measured by using the measuring device having bobs and wires coated with a coating material excellent in heat and erosion resistance. Consequently, the density of various melts and liquids is easily measured in a short time with high accuracy according to the present invention. The measured value is effectively used for the stable growth of a crystal free from defects such as dislocations or inclusions.

What is claimed is:

1. A device for measuring the density of a high-temperature melt, comprising
   a weight having a hook to be hung from a suspensor thread extending downwards from a balance,
   a rigid connector extending downwards from said weight, and
   a bob provided at the lower end of said rigid connector.

2. The device according to claim 1, wherein the weight is the same shape and size as the bob.

3. The device according to claim 1, wherein the rigid connector is made of a rigid wire or rod.

4. A device for measuring the density a high-temperature melt, comprising
   a weight having a hook to be hung from a suspensor thread extending downwards from a balance,
   a rigid connector extending downwards from said weight,
   a bob provided at the lower end of said rigid connector, and a protective coating layer formed on at least the surface part of the rigid connector and the bob to be immersed in the melt.

5. The device according to claim 4, wherein the weight is the same shape and size as the bob.

6. The device according to claim 4, wherein the rigid connector is made of a rigid wire or rod.

7. A device for measuring the density of a high-temperature melt, comprising
   a weight having a hook to be hung from a suspensor thread extending downwards from a balance,
   an upper rigid connector extending downwards from said weight,
   an upper bob provided at the lower end of said upper rigid connector,
   a lower rigid connector extending downwards from said upper bob, and
   a lower bob provided at the lower end of said lower rigid connector.

8. The device according to claim 7, wherein the upper and lower connectors are made of a rigid wire or rod.

9. A device for measuring the density of a high-temperature melt, comprising
   a weight having a hook to be hung from a suspensor thread extending downwards from a balance,
   an upper rigid connector extending downwards from said weight, an upper bob provided at the lower end of said upper rigid connector, a lower rigid connector extending downwards from said upper bob, a lower bob provided at the lower end of said lower rigid connector, and a protective coating layer formed on at least the surface part of the rigid connectors and the bobs to be immersed in the melt.

10. The device according to claim 9, wherein the upper and lower rigid connectors are made of a rigid wire or rod.

* * * * *